(12) United States Patent
Matheny

(10) Patent No.: US 9,011,526 B2
(45) Date of Patent: Apr. 21, 2015

(54) TUBULAR EXTRACELLULAR MATRIX PROSTHETIC VALVE

(71) Applicant: CorMatrix Cardiovascular, Inc, Roswell, GA (US)

(72) Inventor: Robert G Matheny, Norcross, GA (US)

(73) Assignee: CorMatrix Cardiovascular, Inc, Roswell, GA (US)

( * ) Notice: Subject to any disclaimer, the term of this patent is extended or adjusted under 35 U.S.C. 154(b) by 0 days.

(21) Appl. No.: 14/502,038

(22) Filed: Sep. 30, 2014

(65) Prior Publication Data

US 2015/0032205 A1    Jan. 29, 2015

Related U.S. Application Data

(63) Continuation-in-part of application No. 13/804,683, filed on Mar. 14, 2013.

(51) Int. Cl.
*A61F 2/24* (2006.01)
*A61L 27/36* (2006.01)
*A61L 27/54* (2006.01)

(52) U.S. Cl.
CPC ........... *A61F 2/2412* (2013.01); *A61L 27/3633* (2013.01); *A61L 27/3629* (2013.01); *A61L 27/54* (2013.01); *A61F 2220/0075* (2013.01); *A61L 2300/252* (2013.01); *A61L 2300/216* (2013.01); *A61L 2300/40* (2013.01); *A61L 2430/20* (2013.01); *A61F 2/2415* (2013.01)

(58) Field of Classification Search
CPC ....... A61F 2/24; A61F 2/2412; A61F 2/2415; A61F 2/2469; A61F 2220/0075; A61L 27/3629; A61L 27/3633; A61K 35/12
See application file for complete search history.

(56) References Cited

U.S. PATENT DOCUMENTS 6,126,686 A  * 10/2000  Badylak et al. ............... 623/1.24
2014/0277416 A1 *  9/2014  Matheny ...................... 623/2.15

* cited by examiner

*Primary Examiner* — Randy Shay
(74) *Attorney, Agent, or Firm* — Francis Law Group

(57) ABSTRACT

A seamless prosthetic valve having an outer abluminal surface, a triple walled intermediate portion, and at least one valve leaflet that is configured to selectively restrict fluid flow through the valve, the valve leaflet being formed by suturing the triple walled intermediate portion at a first commissure connection point.

15 Claims, 10 Drawing Sheets

TUBULAR EXTRACELLULAR MATRIX PROSTHETIC VALVE

CROSS-REFERENCES TO RELATED APPLICATIONS

This application is a continuation-in-part of U.S. application Ser. No. 13/804,683, filed on Mar. 14, 2013.

FIELD OF THE INVENTION

The present invention generally relates to prosthetic valves for replacing defective cardiovascular valves. More particularly, the present invention relates to seamless tubular extracellular matrix (ECM) prosthetic valves for replacing defective aortic, pulmonary, mitral, tricuspid and/or peripheral venous valves, and methods for forming same.

BACKGROUND OF THE INVENTION

As is well known in the art, the human heart has four valves that control blood flow circulating through the human body. On the left side of the heart is the mitral valve, located between the left atrium and the left ventricle, and the aortic valve, located between the left ventricle and the aorta. Both of these valves direct oxygenated blood from the lungs into the aorta for distribution through the body.

The tricuspid valve, located between the right atrium and the right ventricle, and the pulmonary valve, located between the right ventricle and the pulmonary artery, however, are situated on the right side of the heart and direct deoxygenated blood from the body to the lungs.

The peripheral venous system also includes a number of valves that prevent retrograde blood flow. By preventing retrograde blood flow, the valves found throughout the venous system assist the flow of blood through the veins and returning to the heart.

Normally, the mitral valve has two leaflets and the tricuspid valve has at least two, preferably three leaflets. The aortic and pulmonary valves, however, have normally at least two, preferably three leaflets, also often referred to as "cusps" because of their half-moon like appearance.

Venous valves are usually of the bicuspid type, with each cusp or leaflet forming a reservoir for blood, which, under pressure, forces the free edges of the cusps together to permit mostly antegrade blood flow to the heart. As discussed in detail below, since a majority of venous blood flow is against gravity while a person is standing, incompetent or destroyed venous valves can cause significant medical problems in the legs, ankles, and feet.

Valve diseases are typically classified into two major categories; stenosis and insufficiency. In the case of a stenosis, the native valve does not open properly, whereby insufficiency represents the opposite effect showing deficient closing properties.

Insufficiency of the inlet (atrioventricular) tricuspid valve to the right ventricle of the heart results in regurgitation of blood back into the right atrium, which, serving to receive blood flow returning in the veins from the entire body, then results in turn in suffusion and swelling (edema) of all the organs, most notably in the abdomen and extremities, insufficient forward conduction of blood flow from the right ventricle into the lungs causing compromise of pulmonary function, and ultimately pump failure of the right heart. Collectively these conditions are termed right heart failure, a condition that leads to incapacity and possibly to death if progressive and uncorrected.

Insufficiency of vein function due to the incompetence or destruction of peripheral venous valves leads to acute then chronic swelling of the veins and their dependent lymphatics and tissues. This condition can affect the deep veins of the body, commonly the lower extremities or pelvis, or the superficial veins of the lower extremities in particular, leading to progressive expansion of the veins and further valvular incompetence, a condition known as varicose veins.

Medical conditions like high blood pressure, inflammatory and infectious processes often lead to stenosis and insufficiency. Treatment of heart valve dysfunctions typically include reparation of the diseased heart valve with preservation of the patient's own valve or replacement of the valve with a mechanical or bioprosthetic valve (i.e. "tissue" valve), i.e. a prosthetic valve. Particularly for aortic heart valves, however, it is frequently necessary to introduce a heart valve replacement.

Various prosthetic heart valves have thus been developed for replacement of natural diseased or defective valves. Illustrative are the tubular prosthetic tissue valves disclosed in Applicant's Co-Pending U.S. application Ser. Nos. 13/560,573, 13/782,024 and 13/782,289. A further tubular prosthetic valve is disclosed in U.S. Pat. No. 6,126,686.

A major drawback associated with most tubular prosthetic valves, such as the valves disclosed in U.S. Pat. No. 6,126,686, is that the valves are typically formed from one or more sheets of tissue material, e.g., submucosal tissue, which is initially wrapped around a mandrel to form a tubular structure. The resulting tubular construct thus includes a seam extending the length of the construct, which can, and in many instances will, cause perivalvular leakage.

Various conventional sealing techniques have thus been employed to prevent perivalvular leakage from tubular valve constructs, including suturing, crosslinking, binding with adhesives, etc. Although the noted sealing techniques can be, and most times are, highly effective to seal tubular valve constructs, success of the techniques is highly dependent on the processing techniques and/or processing technician, and/or the skill of the surgeon.

Implantation of a prosthetic valve, including mechanical valves and bioprosthetic valves, also requires a great deal of skill and concentration given the delicate nature of the native cardiovascular tissue and the spatial constraints of the surgical field. It is also critical to achieve a secure and reliable attachment of the valve to host cardiovascular tissue.

Various structures and means have thus also been developed to provide a secure and reliable attachment of a prosthetic valve to host cardiovascular tissue. Most surgical techniques comprise suturing the ends of the valve to the annulus of the cardiovascular vessel.

There are numerous drawbacks and disadvantages associated with suturing a valve to host tissue. A major disadvantage is similarly the high risk of perivalvular leakage.

In application Ser. No. 13/560,573 the tissue valve includes a sewing ring that can be employed to suture the ends of the valve to the annulus of the cardiovascular vessel. Although the use of a sewing ring to secure the valve to a cardiovascular vessel can be, and most times is, highly effective, success of the technique is again still highly dependent on the skill of the surgeon.

There is thus a need to provide "seamless" prosthetic valves that can be readily employed to selectively replace diseased or defective aortic, pulmonary, mitral, tricuspid and peripheral venous valves.

There is also a need to provide prosthetic valves having means for secure, reliable and consistent attachment to cardiovascular vessels.

It is therefore an object of the present invention to provide seamless prosthetic tissue valves that can be readily employed to selectively replace diseased or defective aortic, pulmonary, mitral, tricuspid and peripheral venous valves.

It is another object of the present invention to provide a method for forming seamless prosthetic tissue valves that can be readily employed to selectively replace diseased or defective aortic, pulmonary, mitral, tricuspid and peripheral venous valves It is another object of the present invention to provide seamless prosthetic tissue valves having means for secure, reliable, and consistently highly effective attachment to cardiovascular vessels.

It is another object of the present invention to provide seamless prosthetic tissue valves that substantially reduce or eliminate intimal hyperplasia after intervention in a vessel and the harsh biological responses associated with conventional polymeric and metal valves.

It is another object of the present invention to provide seamless extracellular matrix (ECM) prosthetic tissue valves that induce host tissue proliferation, bioremodeling and regeneration of new tissue and tissue structures with site-specific structural and functional properties.

It is another object of the present invention to provide seamless extracellular matrix (ECM) prosthetic tissue valves that are capable of administering a pharmacological agent to host tissue and, thereby produce a desired biological and/or therapeutic effect.

SUMMARY OF THE INVENTION

The present invention is directed to seamless prosthetic tissue valves that can be readily employed to selectively replace diseased or defective aortic, pulmonary, mitral, tricuspid and peripheral venous valves, and methods for forming same.

In a preferred embodiment of the invention, the seamless prosthetic valves comprise continuous tubular members having first and second ends, a triple walled intermediate portion, and at least one internal valve leaflet, the triple walled intermediate portion being formed by everting the first end of the tubular member over the tubular member to form a double walled first end and a doubled wall portion proximal to and extending from said double walled end, and reverting the first end of the tubular member over the double walled end of the tubular member, the internal valve leaflet being formed by suturing the three walls of the triple walled intermediate portion at a first commissure connection point.

In some embodiments, the three walls of the triple walled intermediate portion are sutured at two commissure connection points to form two valve leaflets therein.

In some embodiments, the three walls of the triple walled intermediate portion are sutured at three commissure connection points to form three valve leaflets therein.

In a preferred embodiment of the invention, the tubular member comprises mammalian small intestine submucosa.

In some embodiments, the small intestine submucosa comprises porcine small intestine submucosa.

In some embodiments of the invention, the tubular member (or material thereof) includes at least one additional biologically active agent or composition, i.e. an agent that induces or modulates a physiological or biological process, or cellular activity, e.g., induces proliferation, and/or growth and/or regeneration of tissue.

In some embodiments, the biologically active agent comprises a protein.

In some embodiments, the biologically active agent comprises a cell.

In some embodiments, the tubular member (or material thereof) includes at least one pharmacological agent or composition (or drug), i.e. an agent or composition that is capable of producing a desired biological effect in vivo, e.g., stimulation or suppression of apoptosis, stimulation or suppression of an immune response, etc.

In some embodiments of the invention, the pharmacological agent comprises an anti-inflammatory agent.

In some embodiments of the invention, the pharmacological agent comprises a statin, i.e. a HMG-CoA reductase inhibitor.

In some embodiments of the invention, the seamless prosthetic valves include at least one anchoring mechanism.

In some embodiments of the invention, the anchoring mechanism comprises at least one reinforcing ring or band that is positioned and secured at a desired position on or in the valve.

In some embodiments of the invention, the anchoring mechanism comprises at least two reinforcing rings that are positioned and secured at desired positions, e.g. proximal and distal ends, on or in the valve.

In a preferred embodiment of the invention, the anchoring mechanisms are designed and configured to position the seamless prosthetic valves proximate the wall of a vessel (i.e. host tissue thereof), and maintain contact therewith, for a predetermined temporary support time period.

In some embodiments of the invention, the support time period is within the process of tissue regeneration.

The seamless prosthetic valves of the invention provide numerous advantages compared to prior art prosthetic valves. Among the advantages are the following:

The provision of seamless prosthetic tissue valves that can be readily employed to selectively replace diseased or defective aortic, pulmonary, mitral, tricuspid and peripheral venous valves The provision of seamless prosthetic tissue valves that substantially reduce or eliminate intimal hyperplasia after intervention in a vessel and the harsh biological responses associated with conventional polymeric and metal valves.

The provision of seamless prosthetic tissue valves that induce host tissue proliferation, bioremodeling and regeneration of new tissue and tissue structures with site-specific structural and functional properties.

The provision of seamless prosthetic tissue valves that are capable of administering a pharmacological agent to host tissue and, thereby produce a desired biological and/or therapeutic effect.

The provision of seamless prosthetic tissue valves that include anchoring mechanisms that temporarily position the valves proximate cardiovascular tissue for a pre-determined period of time.

The provision of seamless prosthetic tissue valves that exhibit optimum mechanical compatibility with vascular structures.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
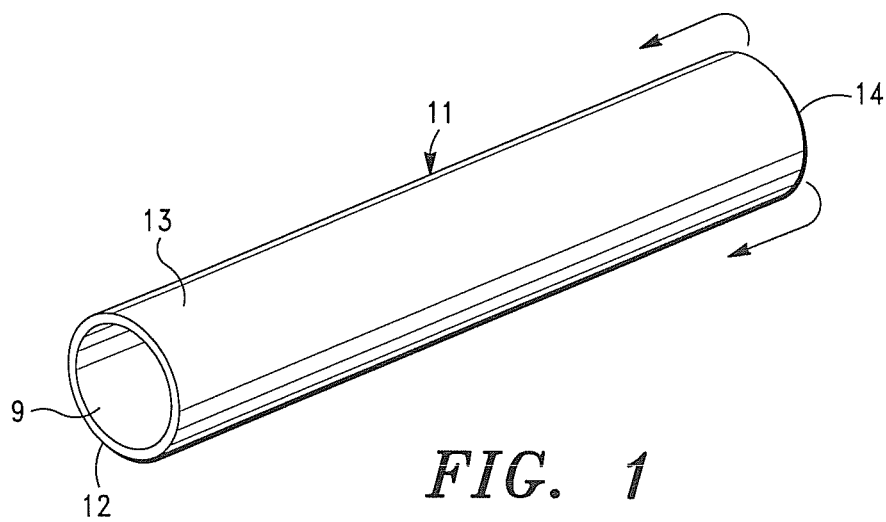
FIG. 1 is a perspective view of one embodiment of a tubular structure that is employed to form a seamless prosthetic valve, in accordance with the invention.
Figure 2:
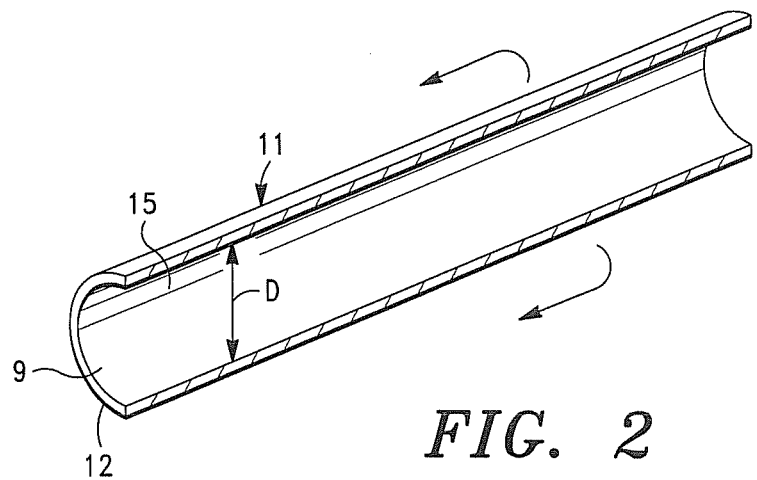
FIG. 2 is a perspective sectional view of the tubular structure shown in FIG. 1 in a first end everted configuration, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "anchoring mechanism" and "anchor", as used herein in connection with some embodiments of the two-piece anchored valves, mean a temporary structure that is configured and employed to "temporarily" position the valve proximate vessel tissue. As discussed in detail herein, in some embodiments of the invention, the anchoring mechanisms are designed and configured to temporarily position tissue valves proximate a recipient's cardiovascular tissue for a predetermined period of time, which, in some embodiments, is preferably within the process of new tissue regeneration.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from epithelium of mesodermal origin, i.e. mesothelial tissue, and basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor alpha (TNA-alpha), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, osteopontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, antiviral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine etidocaine, levobupivacaine, lidocaine/lignocaine, mepivacaine, prilocaine, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide. Chemotherapy agents can also include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isofluopredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, trifiumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to one-piece, seamless prosthetic valves which, in a preferred embodiment, are formed from an extracellular matrix material. According to the invention, the seamless prosthetic valves of the invention can be readily designed and configured and, hence, employed to replace native valves in the body including, without limitation, diseased or defective aortic, pulmonary, mitral, tricuspid and/or peripheral venous valves.

The seamless prosthetic valves of the invention can also be deployed in various cardiovascular vessels by traditional or minimally invasive means.

As discussed in detail herein, in a preferred embodiment, the seamless prosthetic valves comprise continuous tubular structures having first and second ends, a triple walled intermediate portion, and at least one internal valve leaflet, the triple walled intermediate portion being formed by everting the first end of the tubular member over the tubular structure to form a double walled first end and a doubled wall portion proximal to and extending from said double walled end, and reverting the first end of the tubular structures over the double walled end of the tubular construct, the internal valve leaflet being formed by suturing the three walls of the triple walled intermediate portion at a first commissure connection point.

In some embodiments, the three walls of the triple walled intermediate portion are sutured at two commissure connection points to form two valve leaflets therein.

In some embodiments, the three walls of the triple walled intermediate portion are sutured at three commissure connection points to form three valve leaflets therein.

According to the invention, the tubular structures and, hence, seamless prosthetic valves formed therefrom, can comprise various biocompatible materials, including, without limitation, mammalian tissue, e.g., bovine tissue.

In a preferred embodiment of the invention, the tubular structures comprise an extracellular matrix (ECM) material, i.e. ECM tubular structures.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In some embodiments of the invention, the tubular structures comprise small intestine submucosal (SIS) tissue.

In some embodiments of the invention, the tubular structures comprise mesothelial tissue.

In a preferred embodiment, the mammalian tissue source comprises an adolescent mammalian tissue source, i.e. an adolescent mammal, such as a piglet, which is preferably less than three (3) years of age.

In a preferred embodiment, the ECM material is decellularized and, hence, remodelable. According to the invention, the ECM material can be decellularized by various conventional means. In a preferred embodiment, the ECM material is decellularized via one of the unique Novasterilis processes disclosed in U.S. Pat. No. 7,108,832 and Co-Pending U.S. patent application Ser. Nos. 13/480,204 and 13/480,347; which are incorporated by reference herein in their entirety.

As set forth in Co-Pending U.S. application Ser. No. 13/480,347, the ECM material decellularized via the Novasterilis processes has (i) less than 4% DNA content, (ii) a dry weight bFGF content of at least 140 pg/mg, (iii) at least 96% decellurization, and (iv) a tensile strength of at least 9 N. The noted material characteristics, i.e. DNA and bFGF contents, provide an optimum environment for tissue remodeling and regeneration of valve structures. The noted tensile strength, i.e. ≥9 N, also provides a robust valve structure that is more than adequate to meet the force requirements of an AV valve, while retaining sufficient pliability.

The Novasterilis processes also eliminate the need for fixatives, e.g., gluteraldehyde, and conventional sterilization means, such as ethylene oxide (EtO) sterilization, which are often associated with valve calcification after implantation.

According to the invention, when an ECM tubular structure and, hence, prosthetic valve formed therefrom, is implanted in a subject's body, the ECM tubular structure thus induces enhanced "modulated healing" and regeneration of new cardiovascular tissue and valves that have substantially similar structures and perform substantially the same function as native vascular valves.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the ECM tubular structures and, hence, prosthetic valves formed therefrom alter, delay, retard, reduce, and/or detain one or more of the phases associated with healing of damaged tissue, including, but not limited to, the inflammatory phase (e.g., platelet or fibrin deposition), and the proliferative phase.

In some embodiments, "modulated healing" refers to the ability of the ECM tubular structures and, hence, prosthetic valves formed therefrom to alter a substantial inflammatory phase (e.g., platelet or fibrin deposition) at the beginning of the tissue healing process.

The term "modulated healing" also means and includes the ability of the ECM tubular structures and, hence, prosthetic valves formed therefrom to induce host tissue proliferation, bioremodeling, including neovascularization, e.g., vasculogenesis, angiogenesis, and intussusception, and regeneration of tissue structures with site-specific structural and functional properties.

As stated above, in some embodiments of the invention, the tubular structures include at least one exogenously added biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells and proteins.

In some embodiments, the tubular structures include at least one exogenously added pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. Several of the properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

Applicant has further found that the addition of a statin to an ECM tubular structure of the invention, i.e. a tubular structure comprising one of the aforementioned ECM materials, significantly enhances modulated healing.

A significant advantage of administering a statin augmented ECM material (and, hence, ECM tubular structure and seamless prosthetic valves formed therefrom) is that, when an ECM tubular structure is implanted in the body of a subject, the ECM tubular structure and, hence, prosthetic valve formed therefrom, significantly enhances "modulated healing"; specifically, enhanced modulation of inflammatory and proliferative phases, and regeneration of tissue structures with site-specific structural and functional properties.

In some embodiments of the invention, the pharmacological agent comprises chitosan. As also set forth in detail in Co-Pending application Ser. No. 13/573,569, chitosan also exhibits numerous beneficial properties that provide several beneficial biochemical actions or activities.

As also indicated above, in some embodiments of the invention, the seamless prosthetic valves of the invention further include at least one anchoring mechanism that is configured to position the valves proximate cardiovascular tissue, and maintain contact therewith for a pre-determined anchor support time period. According to the invention, the anchoring mechanisms can comprise various forms and materials.

In some embodiments of the invention, the anchoring mechanisms comprise reinforcing rings or bands that are positioned and secured at desired positions, e.g. proximal and distal ends, on or in a seamless prosthetic valve. According to the invention, the reinforcing rings and bands preferably comprise a biocompatible material, such as a biocompatible metal, e.g., Nitinol® and stainless steel, and various polymeric materials. The reinforcing rings and bands can also comprise various biodegradable materials, such as magnesium and ECM material.

As defined above and discussed in detail in Co-pending application Ser. No. 13/782,024, the terms "anchoring mechanism" and "anchor", as used in connection with some embodiments of anchored seamless prosthetic valves of the invention mean a structure that is configured and employed to temporarily position and support a seamless prosthetic valve of the invention proximate host tissue of a vessel.

In some embodiments, the anchoring mechanisms position the anchored seamless valves proximate host tissue of a vessel, and maintain contact therewith for a predetermined temporary anchor support period of time within the process of tissue regeneration.

Referring now to FIGS. 1-4 and 5A-5F, one embodiment of a seamless prosthetic tissue valve and method for forming same will be described in detail.

As indicated above and illustrated in FIGS. 1-4, the seamless prosthetic valves of the invention comprise a continuous tubular structure 11 having a lumen 9 therethrough, outer and inner surfaces 13, 15, and first and second ends 12, 14, a triple walled intermediate portion 20, and, as discussed in detail below, at least one internal valve leaflet that is configured to selectively prevent undesired regurgitation of blood through the valve structure.

According to the invention, the size or operative diameter "D" and length of the tubular structure 11 and, hence, prosthetic valves formed therefrom can vary to accommodate placement in various adult and pediatric cardiovascular vessels.

In a preferred embodiment, the tubular structure lumen 9 has a diameter "D" in the range of 3.0-10.0 mm.

Preferably, the first and second ends 12, 14 of the tubular structure 11 are configured to attach to a native cardiovascular vessel, wherein the lumen 9 is in fluid communication and alignment with the native vessel, e.g., tubular structure end 12 attached to a severed first end of a cardiovascular vessel and tubular structure end 14 attached to a severed second end of the cardiovascular vessel.

As indicated above, in a preferred embodiment of the invention, the tubular structure 11 comprises an extracellular matrix (ECM) material, more preferably, an acellular ECM material derived from one of the aforementioned tissue sources, e.g. small intestine submucosa.

According to the invention, the ECM tubular structure 11 can be derived from various sources. In some embodiments, the ECM tubular structure 11 comprises a section of small intestine from a fetal pig.

In a preferred embodiment, the tubular structure 11 is processed as follows: all cellular remnants, e.g., serosa, subserosa, thick muscle layers, etc., are removed from the tubular structure 11, which results in a rougher outer surface 13, i.e. abluminal surface, and a smoother inner surface 15; the smoother inner surface 15 resulting from the removal of the tunica mucosa.

Applicant has found that the rough abluminal surface 13 of the tubular structure 11 readily attaches to itself and, hence, facilitates effective formation of the two walled end 16 and three walled intermediate portion 20 of the formed valve structure, which is discussed below.

The smooth inner surface 15 of the tubular structure 11 will also be less thrombotic and exhibit enhanced endothelialization.

Figure 3:
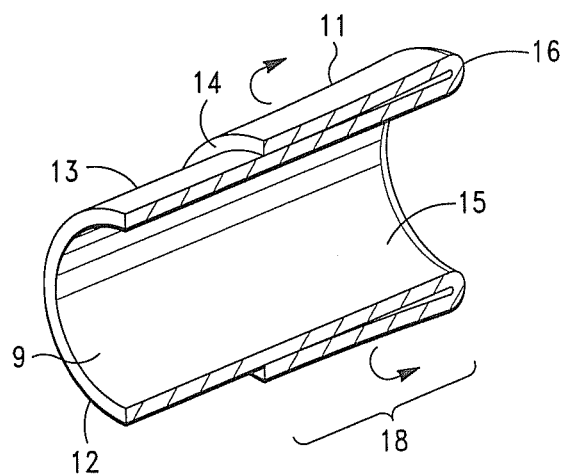
FIG. 3 is a perspective sectional view of the tubular structure shown in FIG. 1 in a first end everted configuration, in accordance with the invention.
Figure 4:
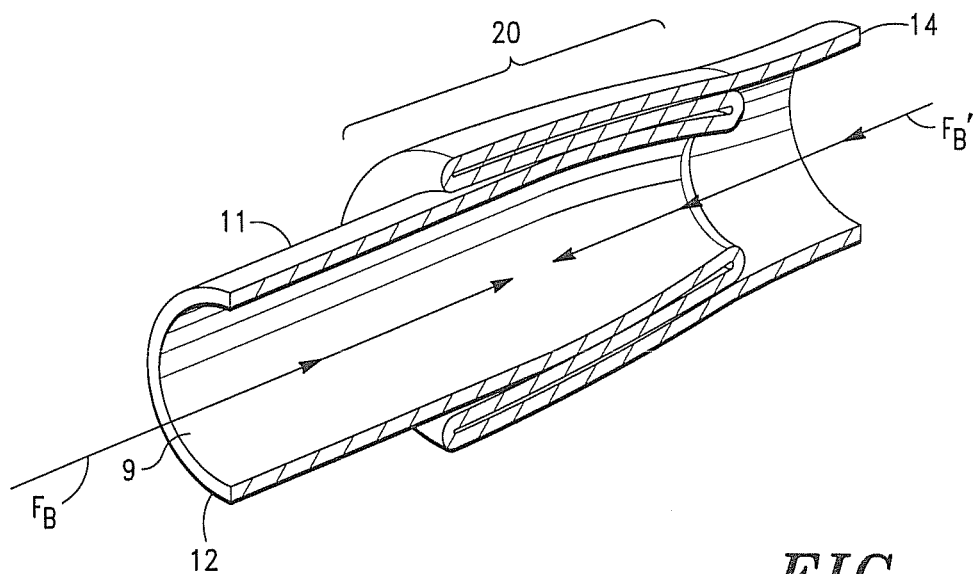
FIG. 4 is a perspective sectional view of the tubular structure shown in FIG. 3 in a first end reverted configuration, wherein the tubular structure has a three wall intermediate section, in accordance with the invention.

According to the invention, the triple walled intermediate portion 20 of the tubular structure 11 is formed by everting the first end of the tubular member 14 over the tubular structure 11, whereby the abluminal surface 13 is in contact with itself and a double walled first end 16 and a doubled wall portion 18 proximal to and extending from said double walled end 16 is formed, as shown in FIG. 3, and reverting the first end 14 of the tubular structure 11 over the double walled end 16 of the tubular structure 11, as shown in FIG. 4.

As indicated above, the seamless prosthetic valves of the invention further comprise at least one internal valve leaflet. As discussed in detail below, in some embodiments of the invention, the prosthetic valves have two internal leaflets. In some embodiments, the prosthetic valves have three leaflets.

According to the invention, the valve leaflets are formed by suturing the three walls of the triple walled intermediate portion 20 at one, two or three commissure connection points.

As discussed in detail below, to provide prosthetic valves having fully functioning valve leaflets, proper placement (or connection) of the tubular structures, and, hence, prosthetic valves formed therefrom to a cardiovascular vessel is essential. Referring to FIG. 4, to provide fully functioning valve leaflets, tubular structure ends 12, 14 are disposed on or in the cardiovascular vessel, whereby, normal blood flow (denoted by Arrow $F_B$) enters into the tubular structure end 12, into and through lumen 9, and out tubular structure end 14 and, whereby, regurgitating blood (denoted by Arrow $F_{B'}$) flows into tubular structure end 14.

Referring now to FIGS. 5A-5E, the formation of a seamless prosthetic valves having two valve leaflets will be described in detail.

Referring first to FIGS. 5A-5D, after the valve structure 11 shown in FIG. 4 is formed, the three walls of the triple walled intermediate portion 20 are sutured along a line at two commissure connection points 22a, 22b to form tubular valve member 10a, having two valve leaflets therein. In a preferred embodiment, the two commissure connection points 22a, 22b are disposed approximately 180° apart, as shown schematically in FIG. 5A.

Figure 5A:
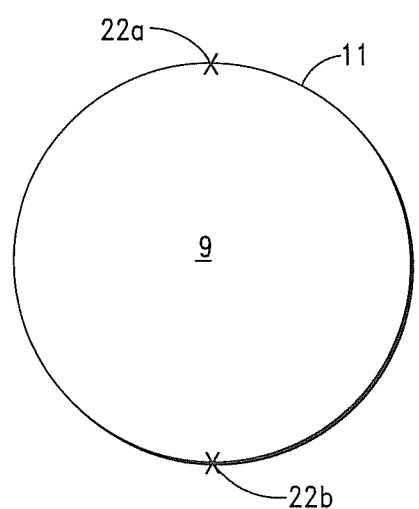
FIG. 5A is a schematic illustration of the tubular structure shown in FIG. 3 showing two commissure connection points, in accordance with the invention.
Figure 5B:
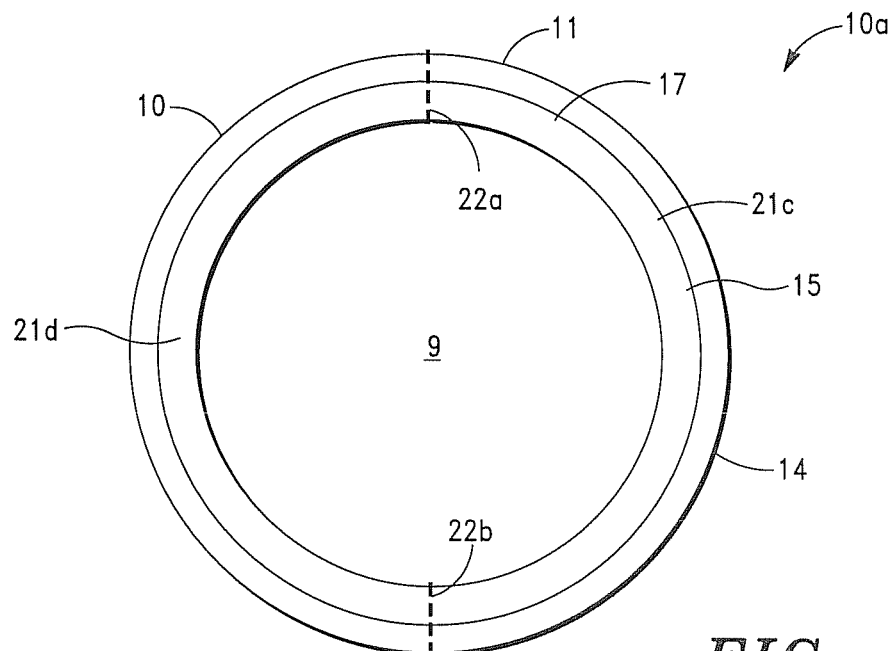
FIG. 5B is an end plan view of the tubular structure shown in FIG. 3 having two commissure connection points, in accordance with the invention.

As illustrated in FIG. 5B, after the three walls of the triple walled intermediate portion 20 are sutured at commissure connection points 22a, 22b, the resulting tubular structure 11 comprises two restrained regions 21a, 21b and two non-connected and, hence, unrestrained regions 21c, 21d of folded over region 17.

Figure 5C:
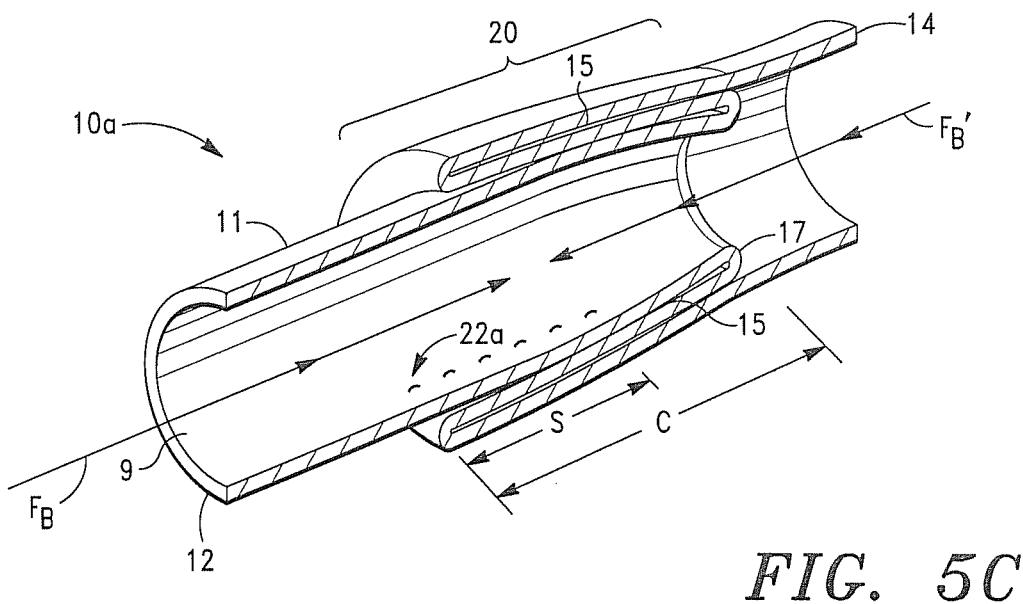
FIGS. 5C and 5D are perspective sectional views of the tubular structure shown in FIG. 5B, in accordance with the invention.
Figure 5D:
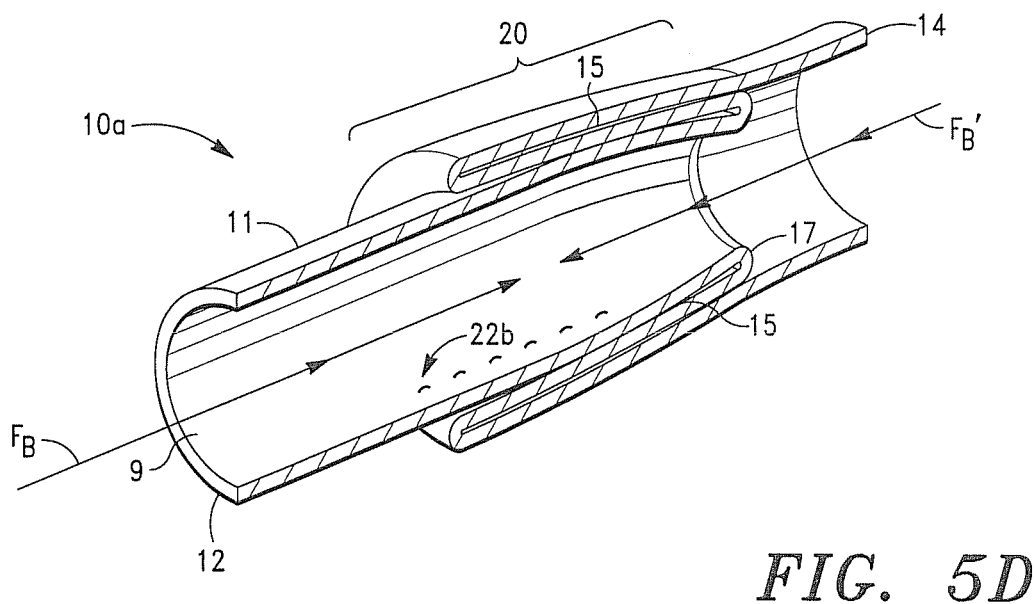
Figure 5E:
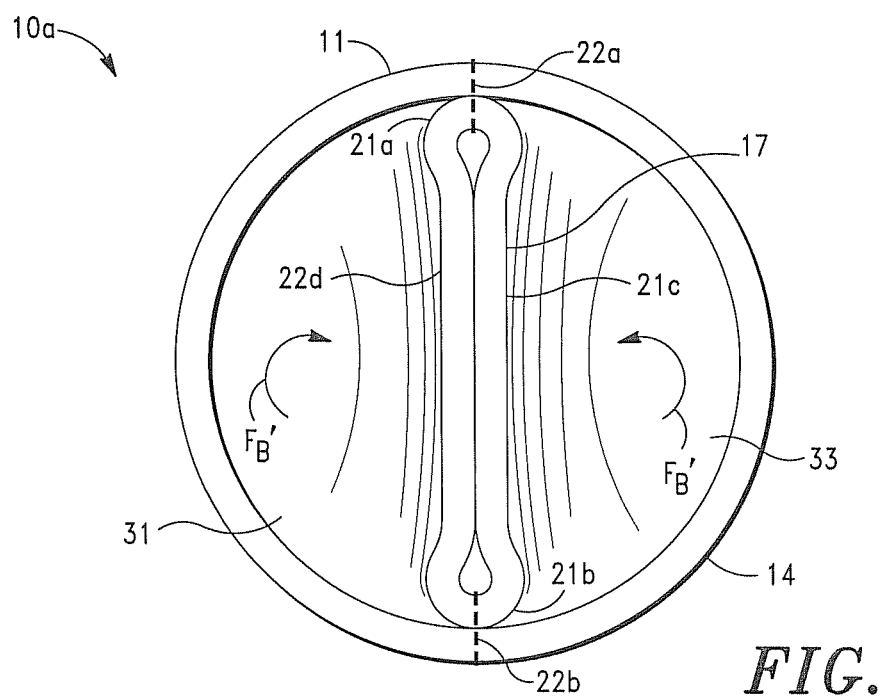
FIG. 5E is an end plan view of the tubular structure shown in FIG. 5B showing the formed valve leaflets in a closed configuration, in accordance with the invention.

As shown in FIG. 5E and discussed below, the restrained regions 21a, 21b and unrestrained regions 21c, 21d form tubular valve construct 10a having two valve leaflets, i.e. valve leaflets 31 and 33.

Referring now to FIGS. 5C and 5D, in a preferred embodiment, each commissure connection point 22a, 22b comprises a sutured region having a suture length "S". In some embodiments, the suture length "S" is preferably in the range of approximately 1.0-5 cm. As will be readily appreciated by one having ordinary skill in the art, the suture length "S" is, however, dependent upon the length of the triple walled intermediate portion 20 (denoted "C").

Thus, in some embodiments, the suture length "S" is at least approximately 50% of the length "C" of the triple walled intermediate portion 20 (or commissure), which provides a suture ratio, i.e. C:S, of at least approximately 2:1. In a preferred embodiment, the suture length "S" comprises approximately 80% of the length "C" of the triple walled intermediate portion 20.

According to the invention, during normal blood flow through the tubular valve construct 10a (in the direction denoted by Arrow $F_B$), the unrestrained regions 21c, 21d of the valve leaflets 31, 33 remain proximate the wall (denoted "15") between the folded over region 17 and outer layer of the three walled region 20, as illustrated in FIGS. 5B and 5D.

Figure 5F:
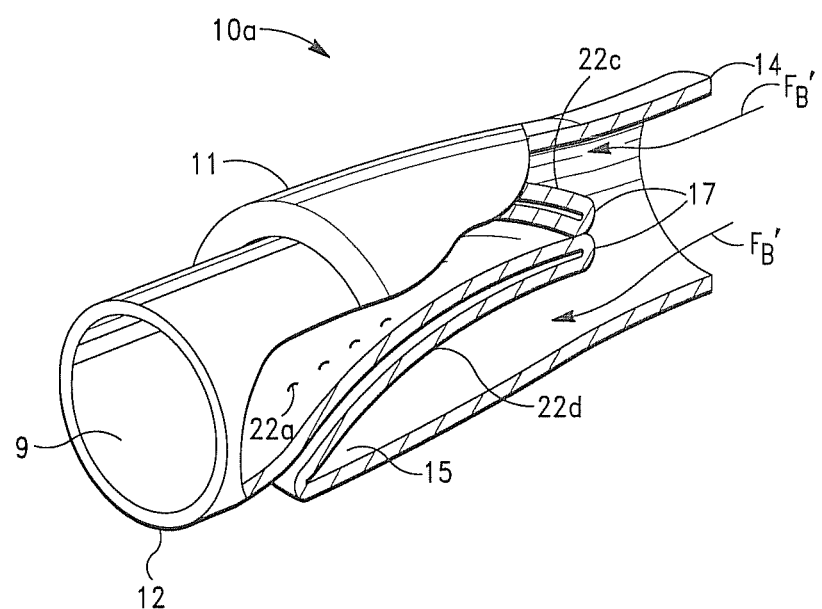
FIG. 5F is a perspective partial sectional view of the tubular structure shown in FIG. 5B further showing the formed valve leaflets in a closed configuration, in accordance with the invention.

As illustrated in FIGS. 5E and 5F, when the tubular valve construct 10a is subjected to regurgitating blood flow in the direction denoted by Arrow $F_{B'}$, the unrestrained regions 21c, 21d of the valve leaflets 31, 33 deflect inward toward the center of the valve lumen 9 as a result of the regurgitating blood flow $F_{B'}$ proximate the wall 15 between the folded over region 17 and outer layer of the three walled region 20, wherein the valve leaflets 31, 33 restrict regurgitating blood flow through the valve lumen 9.

Referring now to FIGS. 6A-6D, the formation of a seamless prosthetic valves having three valve leaflets will be described in detail.

After the valve structure 11 shown in FIG. 4 is formed, the three walls of the triple walled intermediate portion 20 are sutured along a line at three commissure connection points 22a, 22b, 22c to form tubular valve member 10b, having three valve leaflets therein. In a preferred embodiment, the three commissure connection points 22a, 22b, 22c are substantially equally spaced around the circumference of the tubular structure 11, as shown schematically in FIG. 6A.

Figure 6A:
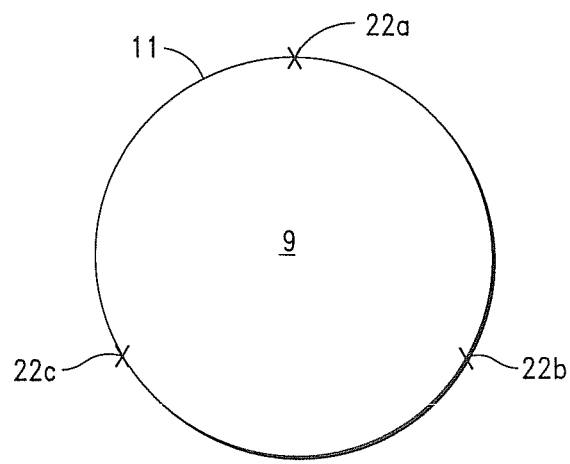
FIG. 6A is a schematic illustration of the tubular structure shown in FIG. 3 showing three commissure connection points, in accordance with the invention.
Figure 6B:
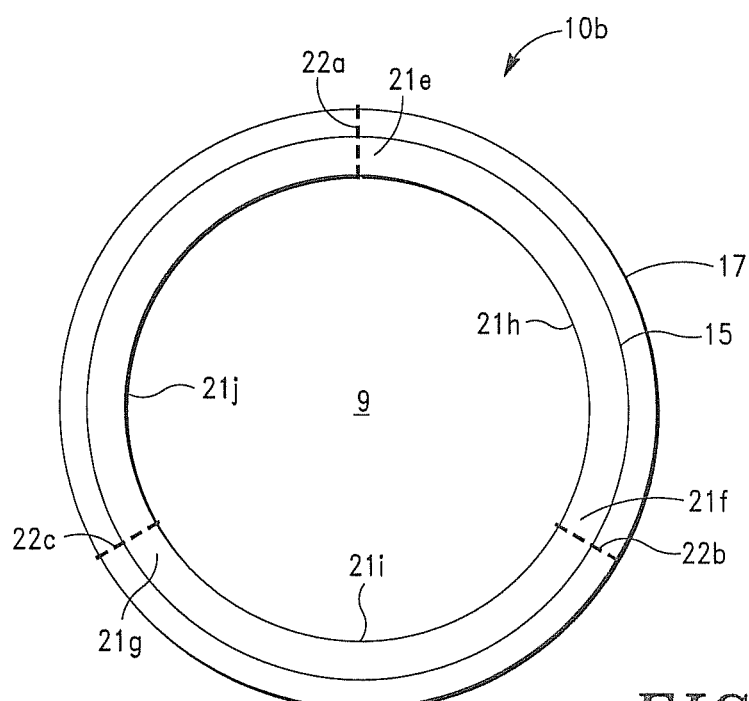
FIG. 6B is an end plan view of the tubular structure shown in FIG. 3 having three commissure connection points, in accordance with the invention.
Figure 6C:
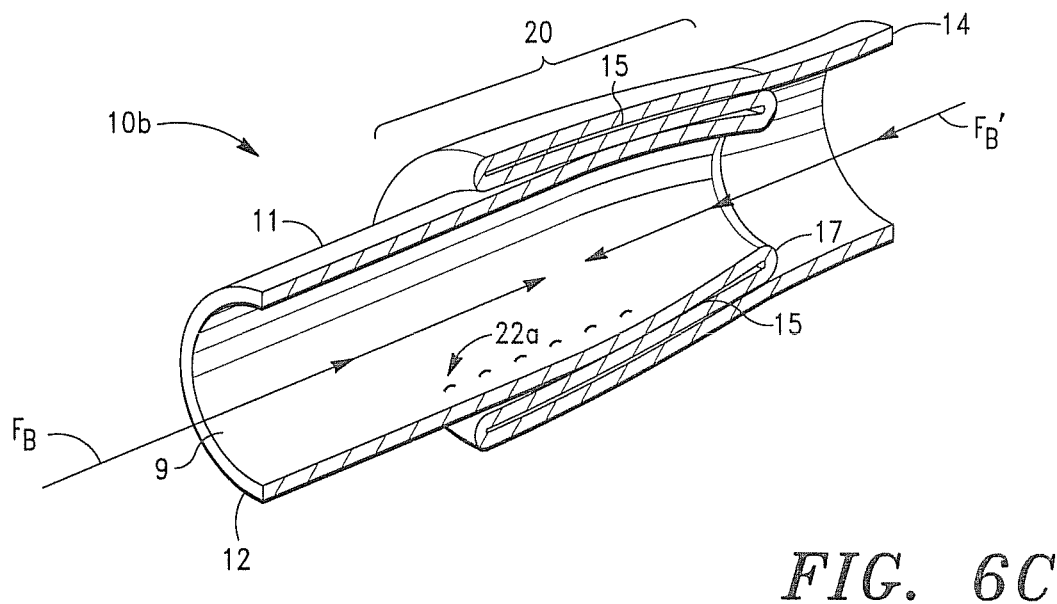
FIGS. 6C-6E are perspective sectional views of the tubular structure shown in FIG. 6B, in accordance with the invention.
Figure 6D:
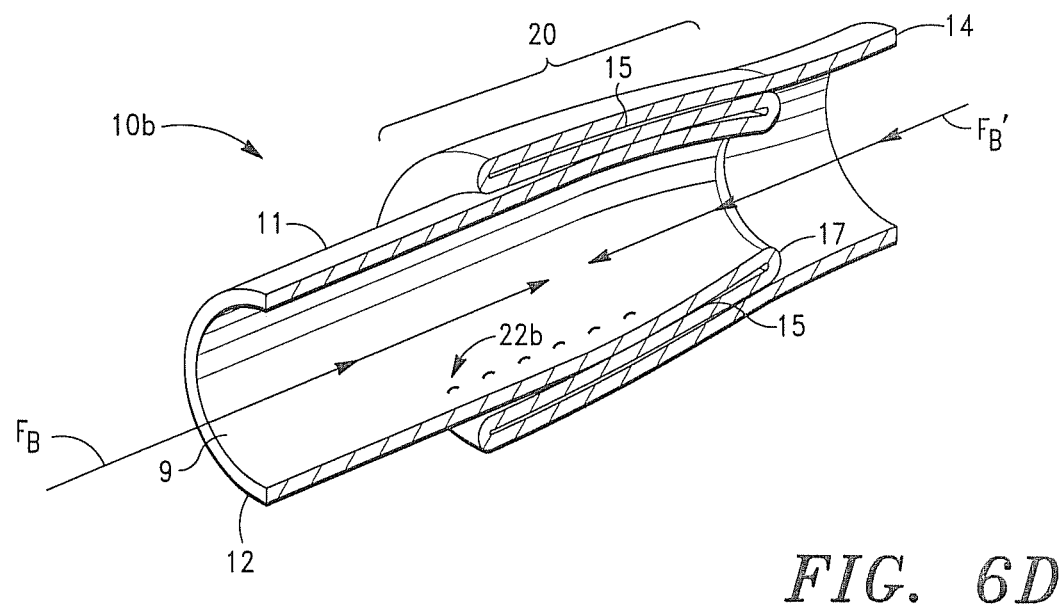
Figure 6E:
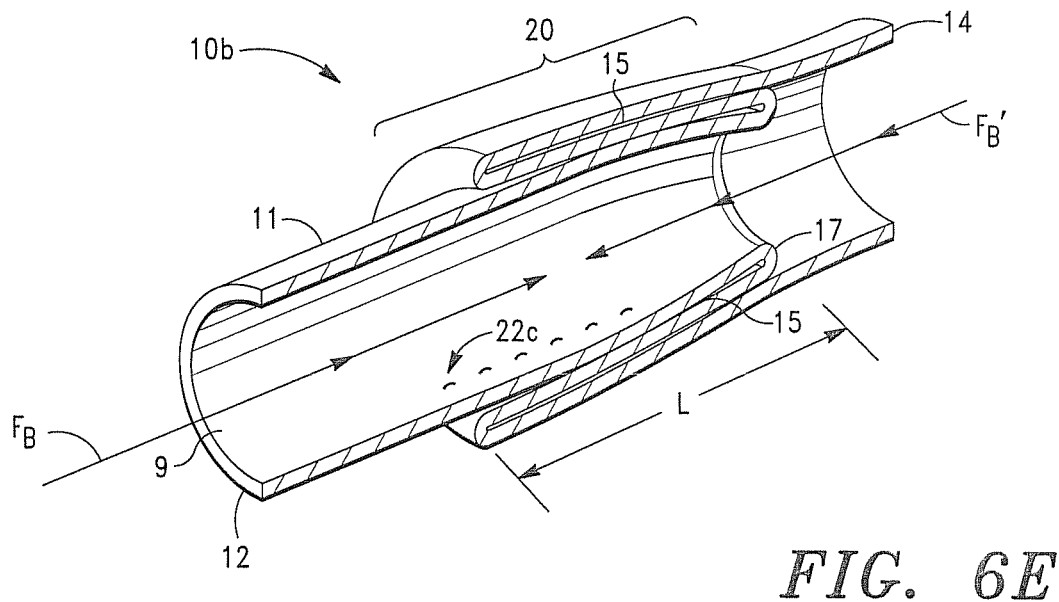

As illustrated in FIG. 6B, after the three walls of the triple walled intermediate portion 20 are sutured at commissure connection points 22a, 22b, 22c the resulting tubular structure 11 comprises three restrained regions 21e, 21f, 21g and three non-connected and, hence, unrestrained regions 21h, 21i, 21j of folded over region 17.

Figure 6F:
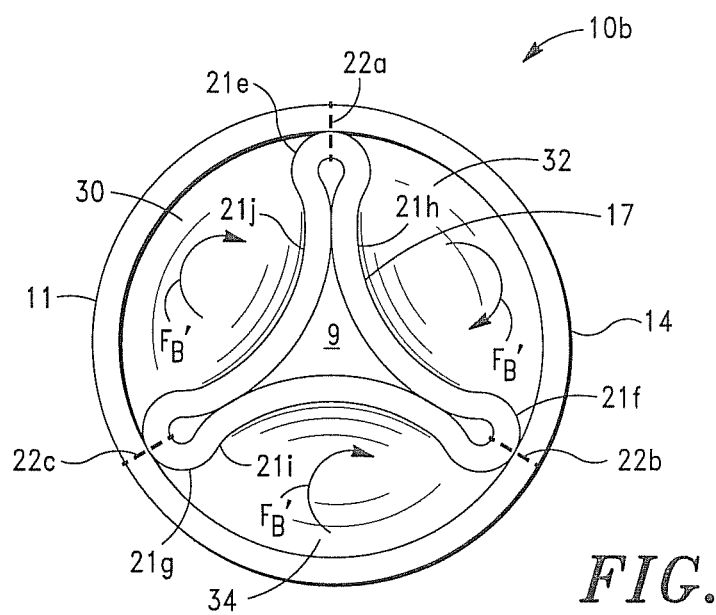
FIG. 6F is an end plan view of the tubular structure shown in FIG. 6B showing the formed valve leaflets in a closed configuration, in accordance with the invention.

As shown in FIG. 6F and discussed below, the restrained regions 21e, 21f, 21g and unrestrained regions 21h, 21i, 21j form tubular valve construct 10b having three valve leaflets, i.e. valve leaflets 30, 32, and 34.

According to the invention, during normal blood flow through the tubular valve construct 10b (in the direction denoted by Arrow $F_B$), the unrestrained regions 21h, 21i, 21j of the valve leaflets 30, 32 and 34 similarly remain proximate the wall (denoted "15") between the folded over region 17 and outer layer of the three walled region 20, as illustrated in FIGS. 6B-6E.

As illustrated in FIG. 6F, when the tubular valve construct 10b is subjected to regurgitating blood flow in the direction denoted by Arrow $F_{B'}$, the unrestrained regions 21h, 21i, 21j of valve leaflets 30, 32 and 34 similarly deflect inward toward the center of the valve lumen 9 as a result of the regurgitating blood flow $F_{B'}$ proximate the wall 15 between the folded over region 17 and outer layer of the three walled region 20, wherein the valve leaflets 30, 32 and 34 restrict regurgitating blood flow through the valve lumen 9.

Figure 7:
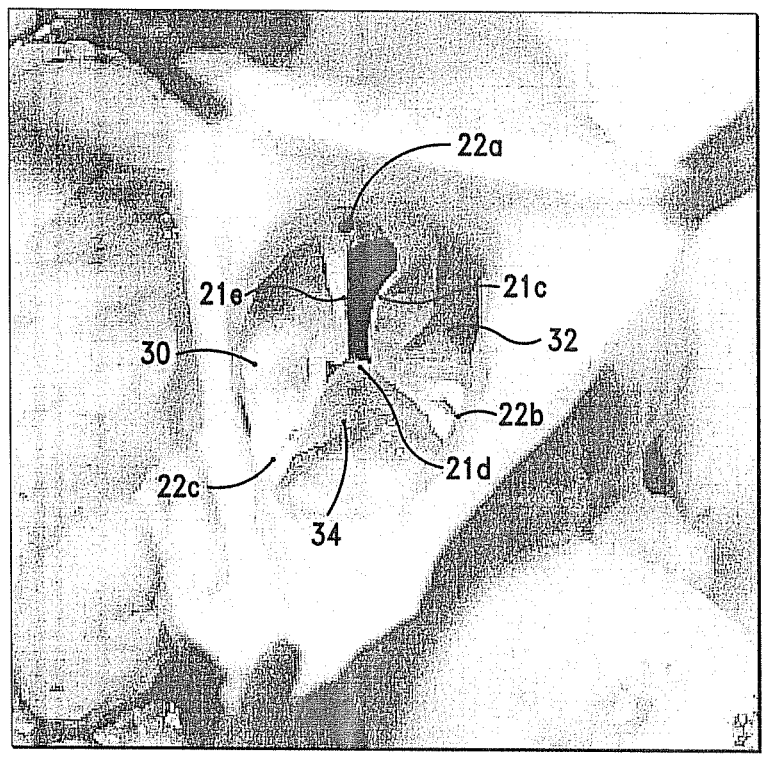
FIG. 7 is an image of a regenerated tri-cusped valve twelve (12) weeks after the tubular structure shown in FIG. 6B was implanted in a mammal, in accordance with the invention.

As indicated above, when the ECM tubular constructs (or valves) 10a, 10b are implanted in a subject's body, the constructs induce "modulated healing" and regeneration of new cardiovascular tissue and valves that have substantially similar structures and perform substantially the same function as native vascular valves. The ECM tubular constructs 10a, 10b thus provide ideal prosthetic templates for optimum regeneration of vascular valves that have substantially similar structures and perform substantially the same function as native vascular valves. Illustrative is the image shown in FIG. 7 of a regenerated tri-cusped valve twelve (12) weeks after implantation in a mammal, showing regenerated valve leaflets 30, 32, 34. (The reference numerals shown in FIG. 7 have been included in the image to show the original commissure connection points 22a, 22b, 22c and unrestrained regions 21a, 21b, 22c of the regenerated valve.)

According to the invention, the leaflets 31, 33 and 30, 32, 34 can have various shapes and sizes, such as shown in U.S. Pat. No. 8,257,434 and Co-pending application Ser. No. 13/560,573, which are incorporated by reference herein.

The size and shape each leaflet is, of course, dependent upon the commissure connection points, i.e. suture length "S" and/or suture ratio, discussed above, and the size, i.e. operative diameter (denoted "D" in FIG. 2), of the tubular structure 11 and, hence, valve formed therefrom.

In some embodiments, the edge length of each leaflet 30, 32, 34 ranges from approximately 10 mm to approximately 70 mm, more preferably from approximately 15 mm to approximately 60 mm, and most preferably from approximately 25 mm to approximately 45 mm. In this aspect, it is contemplated that the ratio between the edge length of each leaflet to the diameter of a target annulus can range from approximately 0.5:1 to approximately 3:1, and, more preferably, from approximately 1:1 to approximately 2:1. In addition to the noted ratios serving as the endpoints of the ranges set forth above, the disclosed ranges also include all ratios falling between the endpoint ratios.

Figure 8:
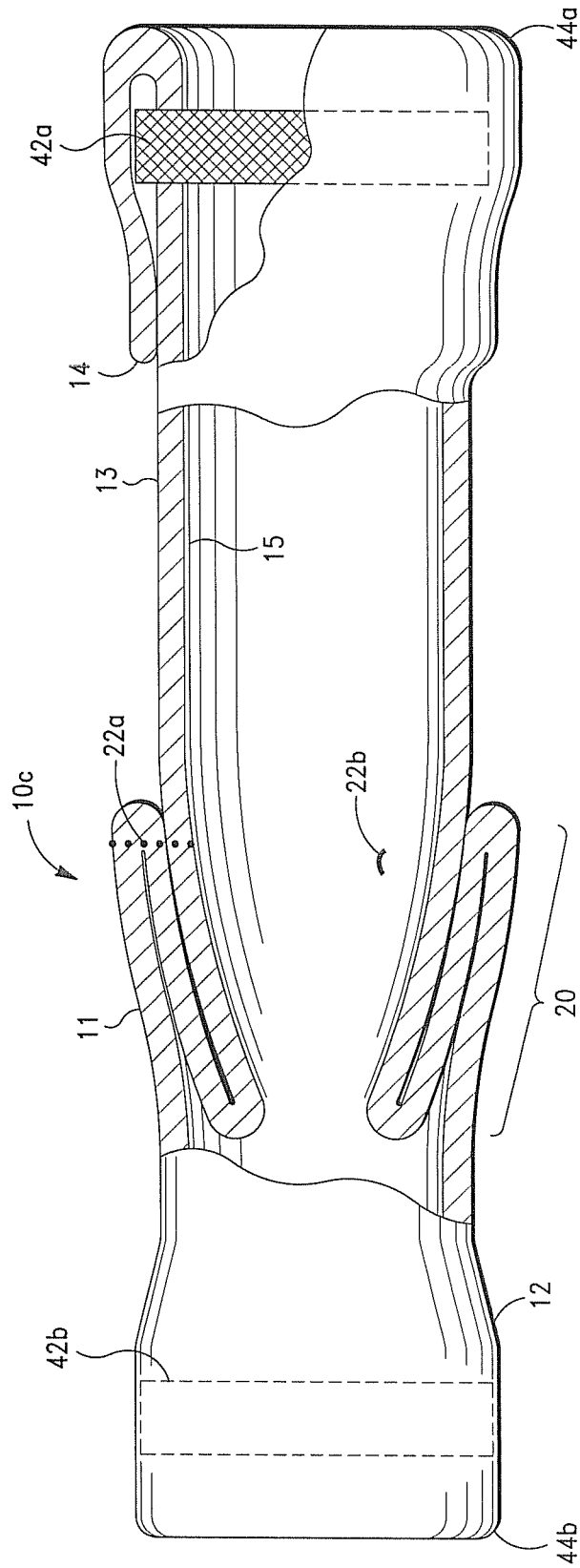
FIG. 8 is a side plan, partial sectional view of an anchored seamless prosthetic valve, in accordance with the invention.

Referring now to FIG. 8, in some embodiments of the invention, the ECM tubular construct 10c further includes at least one anchoring mechanism, more preferably, two anchoring mechanisms 42a, 42b.

As illustrated in FIG. 8, in some embodiments, the anchoring mechanisms 42a, 42b comprise reinforcing rings or bands, which, in the illustrated embodiment, are positioned and secured at proximal 44a and distal 44b ends on the ECM tubular construct 10c.

According to the invention, the anchoring mechanism 42a, 42b can be disposed at other positions in or on the ECM tubular construct 10c.

As set forth in detail in Co-pending application Ser. No. 13/782,024, the anchoring mechanisms 42a, 42b are designed and configured to position the ECM tubular construct 10c proximate host tissue of a vessel, and maintain contact therewith for a predetermined anchor support period of time.

As will readily be appreciated by one having ordinary skill in the art, the present invention provides numerous advantages compared to prior art prosthetic valves. Among the advantages are the following:

The provision of seamless prosthetic tissue valves that can be readily employed to selectively replace diseased or defective aortic, pulmonary, mitral, tricuspid and peripheral venous valves.

The provision of seamless prosthetic tissue valves that substantially reduce or eliminate intimal hyperplasia after intervention in a vessel and the harsh biological responses associated with conventional polymeric and metal valves.

The provision of seamless prosthetic tissue valves that induce host tissue proliferation, bioremodeling and regeneration of new tissue and tissue structures with site-specific structural and functional properties.

The provision of seamless prosthetic tissue valves that are capable of administering a pharmacological agent to host tissue and, thereby produce a desired biological and/or therapeutic effect.

The provision of seamless prosthetic tissue valves that include anchoring mechanisms, which temporarily position the valves proximate cardiovascular tissue for a pre-determined period of time.

The provision of seamless prosthetic tissue valves that exhibit optimum mechanical compatibility with vascular structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve, comprising:
   a continuous tubular structure having an inner lumen, outer abluminal surface, first and second ends, a triple walled intermediate portion, and first and second valve leaflets, said tubular structure comprising extracellular matrix (ECM) from a mammalian tissue source,
   said first and second valve leaflets being configured to transition from a first position, wherein fluid flow in a first direction through said prosthetic valve is unrestricted, to a second position, wherein fluid flow in a second direction through said prosthetic valve is restricted,
   said triple walled intermediate portion being formed by everting said first end of said tubular structure over said tubular structure to form a double walled first end and a doubled wall portion proximal to and extending from said double walled end, and reverting said first end of said tubular structure over said double walled end of said tubular structure,
   said first and second valve leaflets being formed in said tubular structure lumen by all three walls of suturing said triple walled intermediate portion at two commissure connection lines, wherein said first and second valve leaflets comprise two restrained regions and two unrestrained regions.

2. The prosthetic valve of claim 1, wherein said triple walled intermediate portion is sutured at a third commissure connection line, wherein a third valve leaflet is formed, and wherein said third valve leaflet comprises a third restrained region and a third unrestrained region.

3. The prosthetic valve of claim 1, wherein said ECM comprises small intestine submucosa.

4. The prosthetic valve of claim 1, wherein said ECM includes an exogenously added biologically active agent.

5. The prosthetic valve of claim 4, wherein said biologically active agent comprises a growth factor selected from the group consisting of transforming growth factor alpha (TGF-alpha), transforming growth factor beta (TGF-beta), fibroblast growth factor-2 (FGF-2), basic fibroblast growth factor (bFGF), and vascular epithelial growth factor (VEGF).

6. The prosthetic valve of claim 1, wherein said ECM includes an exogenously added pharmacological agent.

7. The prosthetic valve of claim 6, wherein said pharmacological agent comprises a statin selected from the group consisting of atorvastatin, cerivastatin, fluvastatin, lovastatin, mevastatin, pitavastatin, pravastatin, rosuvastatin and simvastatin.

8. The prosthetic valve of claim 6, wherein said pharmacological agent comprises an anti-arrhythmic agent selected from the group consisting of quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, verapamil, diltiazem, adenosine and digoxin.

9. A prosthetic valve, comprising:
a continuous tubular structure having an inner lumen, outer abluminal surface, first and second ends, a triple walled intermediate portion, and first and second valve leaflets, said tubular structure comprising acellular small intestine submucosa (SIS), said SIS comprising less than 4% DNA content and a dry weight bFGF content of at least 140 pg/mg of said SIS, said SIS further exhibiting at least 96% decellurization and a tensile strength of at least 9 N,
said first and second valve leaflets being configured to transition from a first position, wherein fluid flow in a first direction through said prosthetic valve is unrestricted, to a second position, wherein fluid flow in a second direction through said prosthetic valve is restricted,
said triple walled intermediate portion being formed by everting said first end of said tubular structure over said tubular structure to form a double walled first end and a doubled wall portion proximal to and extending from said double walled end, and reverting said first end of said tubular structure over said double walled end of said tubular structure,
said first and second valve leaflets being formed in said tubular structure lumen by all three walls of suturing said triple walled intermediate portion at two commissure connection lines, wherein said first and second valve leaflets comprise two restrained regions and two unrestrained regions.

10. The prosthetic valve of claim 9, wherein said ECM includes an exogenously added biologically active agent.

11. The prosthetic valve of claim 10, wherein said biologically active agent comprises a growth factor selected from the group consisting of transforming growth factor alpha (TGF-alpha), transforming growth factor beta (TGF-beta), fibroblast growth factor-2 (FGF-2), basic fibroblast growth factor (bFGF), and vascular epithelial growth factor (VEGF).

12. The prosthetic valve of claim 9, wherein said ECM includes an exogenously added pharmacological agent.

13. The prosthetic valve of claim 12, wherein said pharmacological agent comprises a statin selected from the group consisting of atorvastatin, cerivastatin, fluvastatin, lovastatin, mevastatin, pitavastatin, pravastatin, rosuvastatin and simvastatin.

14. A prosthetic valve, comprising:
a continuous tubular structure having an inner lumen, outer abluminal surface, first and second ends, a triple walled intermediate portion, and first and second valve leaflets, said tubular structure comprising mesothelial tissue from a mammalian tissue source,
said first and second valve leaflets being configured to transition from a first position, wherein fluid flow in a first direction through said prosthetic valve is unrestricted, to a second position, wherein fluid flow in a second direction through said prosthetic valve is restricted,
said triple walled intermediate portion being formed by everting said first end of said tubular structure over said tubular structure to form a double walled first end and a doubled wall portion proximal to and extending from said double walled end, and reverting said first end of said tubular structure over said double walled end of said tubular structure,
said first and second valve leaflets being formed in said tubular structure lumen by all three walls of suturing said triple walled intermediate portion at two commissure connection lines, wherein said first and second valve leaflets comprise two restrained regions and two unrestrained regions.

15. A prosthetic valve, comprising:
a continuous tubular structure having an inner lumen, outer abluminal surface, first and second ends, a triple walled intermediate portion, and first, second and third valve leaflets, said tubular structure comprising mesothelial tissue from a mammalian tissue source,
said first, second and third valve leaflets being configured to transition from a first position, wherein fluid flow in a first direction through said prosthetic valve is unrestricted, to a second position, wherein fluid flow in a second direction through said prosthetic valve is restricted,
said triple walled intermediate portion being formed by everting said first end of said tubular structure over said tubular structure to form a double walled first end and a doubled wall portion proximal to and extending from said double walled end, and reverting said first end of said tubular structure over said double walled end of said tubular structure,
said first, second and third valve leaflets being formed in said tubular structure lumen by all three walls of suturing said triple walled intermediate portion at three commissure connection lines, wherein said first, second and third valve leaflets comprise three restrained regions and three unrestrained regions.

* * * * *